(12) United States Patent
Nishimura et al.

(10) Patent No.: US 9,803,168 B2
(45) Date of Patent: Oct. 31, 2017

(54) INCUBATOR

(71) Applicant: SHIBUYA CORPORATION, Kanazawa-shi, Ishikawa (JP)

(72) Inventors: Tetsuya Nishimura, Kanazawa (JP); Masaomi Shioya, Kanazawa (JP); Katsuki Hashimoto, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 0 days.

(21) Appl. No.: 15/005,356

(22) Filed: Jan. 25, 2016

(65) Prior Publication Data

US 2016/0215252 A1   Jul. 28, 2016

(30) Foreign Application Priority Data

Jan. 26, 2015   (JP) .................................. 2015-012362

(51) Int. Cl.
   *C12M 1/00* (2006.01)
   *C12M 1/12* (2006.01)
   *C12M 1/34* (2006.01)

(52) U.S. Cl.
   CPC ............. *C12M 41/14* (2013.01); *C12M 29/00* (2013.01); *C12M 29/04* (2013.01); *C12M 37/02* (2013.01); *C12M 41/34* (2013.01); *C12M 41/40* (2013.01)

(58) Field of Classification Search
   CPC ...... C12M 29/00; C12M 29/04; C12M 37/02; C12M 41/14; C12M 41/34; C12M 41/40
   See application file for complete search history.

(56) References Cited

U.S. PATENT DOCUMENTS

| | | | |
|---|---|---|---|
| 2002/0192812 A1* | 12/2002 | Sheldon | A61L 2/238 435/303.1 |
| 2003/0041572 A1* | 3/2003 | Lohr | B01D 46/0024 55/385.2 |
| 2005/0084420 A1 | 4/2005 | Osawa et al. | |
| 2011/0171424 A1 | 7/2011 | Kliesch et al. | |
| 2012/0083030 A1* | 4/2012 | Busujima | C12M 41/14 435/303.1 |

FOREIGN PATENT DOCUMENTS

| | | |
|---|---|---|
| DE | 10 2004 049 210 A1 | 6/2005 |
| DE | 10 2011 111 754 A1 | 2/2013 |
| JP | 5587629 B2 | 8/2011 |
| WO | WO 2014/079696 A1 | 5/2014 |

OTHER PUBLICATIONS

European Search Report dated May 9, 2016 for corresponding application No. 16152037.4 (8 pages).

* cited by examiner

*Primary Examiner* — Nathan Bowers
*Assistant Examiner* — Lydia Edwards
(74) *Attorney, Agent, or Firm* — Flynn, Thiel, Boutell & Tanis, P.C.

(57) ABSTRACT

An incubator 1 includes a cultivating chamber 4 for cultivating culture in a plurality of containers 3 and a supply device 5 provided outside the cultivating chamber 4 and supplying steam into the cultivating chamber 4 for humidification. The supply device 5 includes a supply chamber 5A in which a tray 42 for reserving water is accommodated and an ultrasonic atomizing device 43 for atomizing water. The water in the tray 42 is easily made into steam by the ultrasonic atomizing device 43, passes through an HEPA filter 45 provided in an opening portion 5B and is supplied into the circulation passage 37 of the cultivating chamber 4.

4 Claims, 1 Drawing Sheet

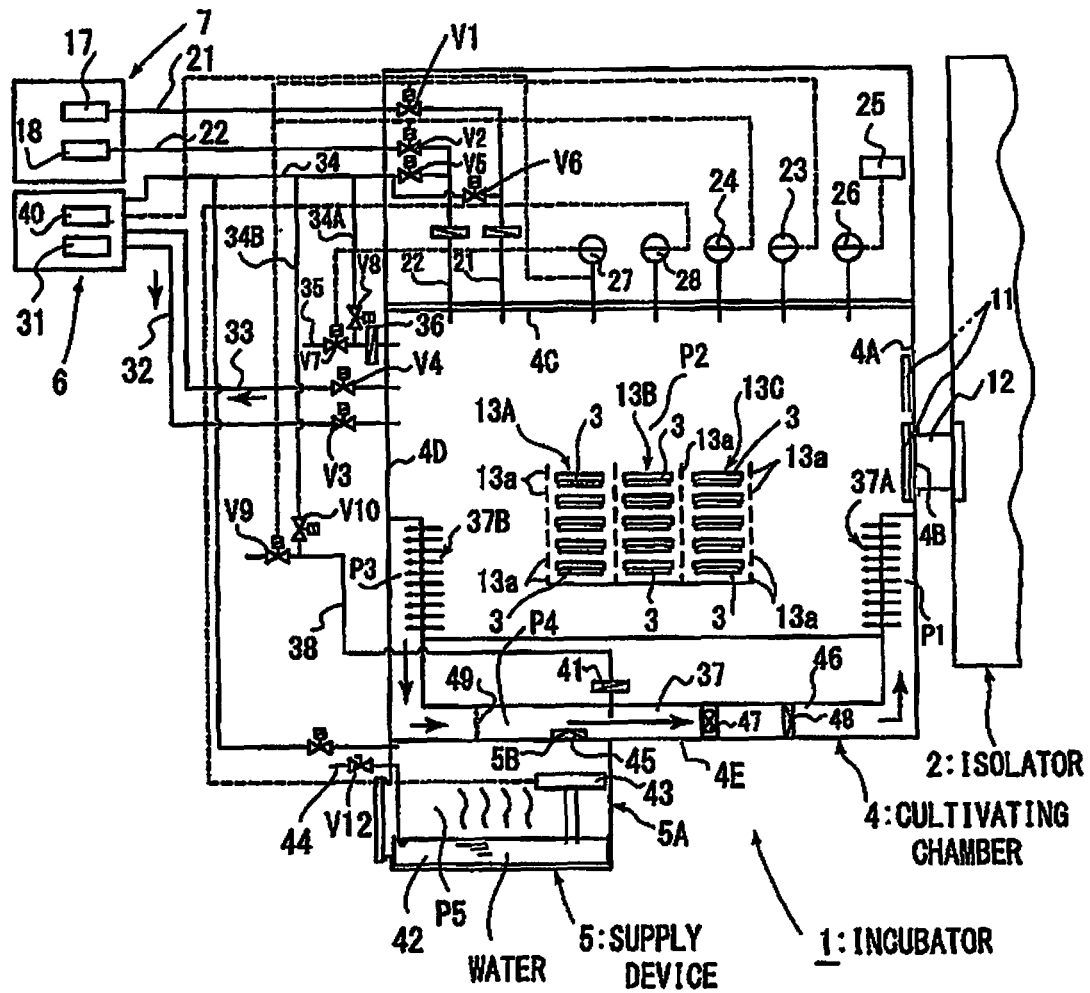

INCUBATOR

FIELD OF THE INVENTION

The present invention relates to an incubator and more particularly to an incubator in which a high humidity is maintained by supplying steam into a cultivating chamber from a supply device provided outside the cultivating chamber.

DESCRIPTION OF THE PRIOR ART

Conventionally, an incubator provided with a cultivating chamber for cultivating a cell by maintaining humidity in the cultivating chamber within a certain range is known (see Patent Literature 1 (Japanese Patent No. 5587629)).

In the prior-art incubator, a tray for reserving water for humidification is disposed in the cultivating chamber, and a pipeline for supplying water for humidification to the tray in the cultivating chamber is provided so that the water is supplied into the tray through the pipeline from a water feed portion installed outside the cultivating chamber and reserved therein and it is evaporated so that the humidity in the cultivating chamber is maintained.

The incubator needs to have an inside of the cultivating chamber kept in an aseptic state in order to prevent contamination of the culture in the cultivating chamber by germs or the like. Thus, in the prior-art incubator, the tray, the pipeline, humidifying means, a sensor, water to be supplied and the like in the cultivating chamber need to take an aseptic measure and a decontamination measure, respectively. Thus, in the prior-art incubator, each device in the cultivating chamber needs to take the aseptic measure and the decontamination measure, which results in a disadvantage that its constitution becomes complicated.

SUMMARY OF THE INVENTION

In view of the aforementioned circumstances, the present invention includes a cultivating chamber for cultivating a culture, a supply device provided outside the cultivating chamber and making reserved water into steam and supplying it into the cultivating chamber, and an air filter provided in a flow passage of the steam from the supply device to the cultivating chamber, characterized in that the steam generated by the supply device is passed through the air filter and then, is supplied into the cultivating chamber so as to humidify an inside of the cultivating chamber.

According to such a constitution, since the steam generated outside the cultivating chamber is supplied into the cultivating chamber through the air filter, there is no need to provide the tray, the humidifying means, a water level sensor and the like in the cultivating chamber, and the cultivating chamber with a constitution simpler than the prior-art one can be provided, and an incubator which can reduce maintenance work can be provided.

Moreover, the inside of the cultivating chamber can be humidified in a more favorable state while germlessness in the cultivating chamber is maintained.

BRIEF DESCRIPTION OF DRAWINGS

FIG. 1 is a constitution diagram illustrating an embodiment of the present invention.

DETAILED DESCRIPTION OF THE EMBODIMENTS

Describing the present invention below regarding an illustrated embodiment, in FIG. 1, reference numeral 1 denotes an incubator for cultivating a culture such as a cell, and an isolator 2 as an aseptic work room is arranged at a position adjacent to this incubator 1.

The incubator 1 of this embodiment has a cultivating chamber 4 storing a plurality of containers 3 to which the culture is made to adhere and cultivating the culture in each of the containers 3, a supply device 5 provided outside the cultivating chamber 4 and supplying steam into the cultivating chamber 4, a decontaminating device 6 for decontaminating the inside of the cultivating chamber 4 and other required spots and adjusting an environment such as a pressure in the cultivating chamber 4, and a gas supply device 7 for supplying a carbon dioxide gas ($CO_2$) and a nitrogen gas ($N_2$) into the cultivating chamber 4.

The cultivating chamber 4 is made of a housing capable of being sealed, an opening portion 4B is formed in a wall surface 4A which is an isolator 2 side, and this opening portion 4B is constituted to be opened/closed by a shutter 11 elevated up/down by an elevating mechanism. The opening portion 4B is connected to the inside of the isolator 2 through a tubular connecting portion 12 while maintaining airtightness. When the shutter 11 is opened, the inside of the isolator 2 and the inside of the cultivating chamber 4 are made to communicate with each other through the connecting portion 12, while when the shutter 11 is closed, the opening portion 4B is closed while maintaining airtightness, and the communication between the cultivating chamber 4 and the isolator 2 is prevented.

In the cultivating chamber 4, three storage cabinets 13A to 13C, each provided with a large number of racks 13a for storing the containers 3, are provided.

The storage cabinets 13A to 13C are formed having the same dimension and the same shape and being vertically long and include a predetermined number of racks 13a at an equal pitch in a vertical direction. In each of these storage cabinets 13A to 13C, an opening for loading/unloading the container 3 is provided and it has such a constitution that each has no side wall covering the periphery and each rack 13a is exposed. Moreover, these storage cabinets 13A and 13C are arranged concentrically in a fan shape adjacent to each other, and loading/unloading of the container 3 to/from each rack 13a is performed by a robot hand, not shown.

The inside of the cultivating chamber 4 is decontaminated by the decontaminating device 6 and then, a carbon dioxide gas and a nitrogen gas are supplied by the gas supply device 7, and concentrations of the nitrogen gas, an oxygen gas, and the carbon dioxide gas in the cultivating chamber 4 are maintained to concentrations suitable for cultivation of the cells in the container 3. Moreover, in order to prevent inflow of external atmosphere, the inside of the cultivating chamber 4 is adjusted to a predetermined pressure by the decontaminating device 6, and the cultivating chamber 4 is maintained at a pressure more positive than the outside. Moreover, a temperature, humidity and the like in the cultivating chamber 4 are also maintained at values suitable for cultivation of the cells in the container 3.

As described above, germlessness is maintained in the cultivating chamber 4 and is also maintained in an environment suitable for cultivation, and by storing the containers 3 to which the culture adheres in the storage cabinets 13A to 13C for a required time, the culture in each of the containers 3 can be cultivated.

Here, a carrying-in work of the container 3 from the isolator 2 to the incubator 1 and a carrying-out work of the container 3 after completion of the cultivation from the incubator 1 to the isolator 2 will be described.

That is, in the isolator 2, transfer of the culture or a medium replacement work in each container 3 is performed by the robot hand, not shown, or manually by an operator. In the isolator 2, the container 3 for which the transfer work of the culture or the medium replacement work has been finished is conveyed into the connecting portion 12 and placed therein.

Then, on the cultivating chamber 4 side, the shutter 11 is opened by the elevating mechanism and the container 3 in the connecting portion 12 is held by the robot hand, not shown, and then, carried into the cultivating chamber 4 and moreover, stored on the required rack 13a in the storage cabinets 13A to 13C. When the container 3 has been carried into the cultivating chamber 4, the shutter 11 is closed so that the opening portion 4B is sealed. Even if the environment in the cultivating chamber 4 is changed by opening of the shutter 11, control is executed so that the environment suitable for cultivation is maintained.

After being stored on the racks 13a of the storage cabinets 13A to 13C for required time, when cultivation of the culture in the container 3 is completed, each container 3 in which cultivation has been completed is taken out of the required rack 13a by the robot hand, not shown, and returned to the connecting portion 12 through the opening portion 4B in which the shutter 11 is opened by the elevating mechanism.

Constitutions of the gas supply device 7 and the decontaminating device 6 will be described. The gas supply device 7 for supplying two kinds of gas into the cultivating chamber 4 includes a supply source 17 of the nitrogen gas ($N_2$) and a pipe 21 for allowing the supply source 17 and the cultivating chamber 4 to communicate with each other, and a supply source 18 of the carbon dioxide gas ($CO_2$) and a pipe 22 for allowing the supply source 18 and the cultivating chamber 4 to communicate with each other are provided.

In the middle of the pipe 21, a normally-closed electromagnetic opening/closing valve V1 is provided, and a normally-closed electromagnetic opening/closing valve V2 is also provided on the other pipe 22. An operation of each of the supply sources 17 and 18 and both electromagnetic opening/closing valves V1 and V2 are configured to be controlled by a controller, not shown. When the controller opens the electromagnetic opening/closing valve V1 and operates the supply source 17, the nitrogen gas is supplied to the cultivating chamber 4. Moreover, when the controller opens the electromagnetic valve V2 and operates the supply source 18, the carbon dioxide gas is supplied to the cultivating chamber 4.

On a top surface 4C of the cultivating chamber 4, an oxygen gas sensor 23 for detecting the oxygen gas concentration in the cultivating chamber 4 is arranged, and a carbon dioxide gas sensor 24 for detecting the concentration of the carbon dioxide gas (CM in the cultivating chamber 4 is arranged. The oxygen gas concentration detected by the oxygen gas sensor 23 and the carbon dioxide gas concentration detected by the carbon dioxide gas sensor 24 are configured to be transmitted to the controller.

A heater 25 is connected to the top surface 4C of the cultivating chamber 4 through a pipe so that the inside of the cultivating chamber 4 can be heated from this heater 25 through the pipe. Moreover, a temperature sensor 26 for detecting a temperature in the cultivating chamber 4 is provided, and the temperature in the cultivating chamber 4 detected by the temperature sensor 26 is configured to be transmitted to the controller.

On the top surface 4C of the cultivating chamber 4, a pressure sensor 27 for detecting a pressure in the cultivating chamber 4 is provided, and a humidity sensor 28 for detecting the humidity in the cultivating chamber 4 is also provided. The pressure in the cultivating chamber 4 detected by the pressure sensor 27 and the humidity in the cultivating chamber 4 detected by the humidity sensor 28 are configured to be transmitted to the controller.

The decontaminating device 6 includes a supply source 31 of hydrogen peroxide gas ($H_2O_2$) which is a decontaminating medium, a pair of supply pipe 32 and a discharge pipe 33 connecting this supply source 31 and the inside of the cultivating chamber 4 to each other, a decontaminating pipe 34 connecting the pipes 21 and 22 to the supply source 31 for decontaminating the insides of the pipes 21 and 22, and an aseptic air supply source 40.

In the supply pipe 32, a normally-closed electromagnetic opening/closing valve V3 is provided, and in the discharge pipe 33, too, a normally-closed electromagnetic opening/closing valve V4 is provided.

A downstream side of the decontaminating pipe 34 branches to two parts, one branch portion is connected to the pipe 21, while the other branch portion is connected to the pipe 22, and in those branch portions, normally-closed electromagnetic opening/closing valves V5 and V6 are provided, respectively. Operations of these electromagnetic opening/closing valves V3 to V6 are controlled by the controller and are configured to be opened at required time.

In a state in which the shutter 11 is closed, when the controller opens the electromagnetic opening/closing valve V3 and operates the supply source 31, the hydrogen peroxide gas is supplied into the cultivating chamber 4 through the supply pipe 32. The supply pipe 32 also works as a supply pipe for supplying aseptic air from the aseptic air supply source 40 into the cultivating chamber 4, and after that, when the electromagnetic opening/closing valve V3 is kept open for the required time by the controller and the aseptic air supply source is operated for the required time, the aseptic air is supplied into the cultivating chamber 4, and aeration is performed. After that, the electromagnetic opening/closing valve V4 is opened so that air containing the hydrogen peroxide gas in the cultivating chamber 4 is discharged to the outside of the cultivating chamber 4 through the discharge pipe 33. As a result, the inside of the cultivating chamber 4 is decontaminated by the hydrogen peroxide gas. Moreover, when the cultivating chamber 4 is decontaminated, the electromagnetic opening/closing valves V5 and V6 are opened and the hydrogen peroxide gas from the supply source 31 flows and decontaminates the insides of the pipes 21 and 22.

On a wall surface 4D on a side opposite to the isolator 2 in the cultivating chamber 4, one end of a pipe 35 for lowering the pressure in the cultivating chamber 4 is connected, and a filter 36 and a normally-closed electromagnetic opening/closing valve V7 are provided in the middle of the pipe 35. The electromagnetic opening/closing valve V7 is constituted to have its operation controlled by the controller, and by opening the electromagnetic opening/closing valve V7 by the controller at the required time, the pressure in the cultivating chamber 4 which has risen can be lowered. The controller is configured to maintain the pressure in the cultivating chamber 4 to a positive pressure larger than a predetermined value by opening the electromagnetic opening/closing valve V7 at the required time after recognizing the pressure in the cultivating chamber 4 detected by the pressure sensor 27.

The tip end of a branch pipe 34A branching from the middle of the decontaminating pipe 34 is connected to the pipe 35, and a normally-closed electromagnetic opening/closing valve V8 is provided in the middle of the branch pipe 34A. An operation of this electromagnetic opening/closing valve V8 is controlled by the controller, and when the inside of the cultivating chamber 4 is decontaminated as described above, the controller also opens the electromagnetic opening/closing valve V8. Thus, when the cultivating chamber 4 is decontaminated, the hydrogen peroxide gas from the supply source 31 flows through the pipe 35, whereby the inside of the pipe 35 is also decontaminated by the hydrogen peroxide gas.

On the side of a bottom surface 4E in the cultivating chamber 4, a circulation passage 37 which will be described later in detail is formed, and an outside air pipe 38 is provided through this circulation passage 37 to the outside of the cultivating chamber 4. In the middle of the outside air pipe 38 located outside the cultivating chamber 4, a normally-closed electromagnetic opening/closing valve V9 is provided. A tip end of a branch pipe 34B branching from the middle of the decontaminating pipe 34 is connected to the outside air pipe 38, and a normally-closed electromagnetic opening/closing valve V10 is provided in the middle of the branch pipe 34B. Operations of both electromagnetic opening/closing valves V9 and V10 are controlled by the controller, and when the controller opens the electromagnetic opening/closing valve V9 at the required time, outside air can be introduced into the circulation passage 37 through the outside air pipe 38. As a result, the concentrations of the carbon dioxide gas and the nitrogen gas in the cultivating chamber 4 can be lowered. In the middle of the outside air pipe 38, a filter 41 is provided, whereby introduction of dust and the like into the circulation passage 37 can be prevented.

When the inside of the cultivating chamber 4 described above is decontaminated, since the controller opens also the electromagnetic opening/closing valve V10, the hydrogen peroxide gas flows through the outside air pipe 38 through the branch pipe 34B, and the inside of the outside air pipe 38 is also decontaminated.

The gas supply device 7 and the decontaminating device 6 of this embodiment are constituted as above, and in the state in which the shutter 11 is closed, when the electromagnetic opening/closing valves V3 to V6, V8, V10, and V11 are opened by the controller and the supply source 31 is operated, the inside of the cultivating chamber 4 is decontaminated by the hydrogen peroxide gas. At the same time, the hydrogen peroxide gas also flows through the decontaminating pipe 34 and its branch pipes 34A and 34B, whereby the insides of the pipes 21, 22, and 35 and the outside air pipe 38 are also decontaminated.

During the decontaminating work, the aseptic air is supplied into the cultivating chamber 4 through the supply pipe 32 from the aseptic air supply source 40 as described above, and aeration in the cultivating chamber 4 is performed.

The electromagnetic opening/closing valves V3 to V6, V8, V10, and V11 are closed after this decontaminating work, while the electromagnetic opening/closing valves V1 and V2 are opened by the controller only for the required time and then, they are closed and thus, the nitrogen gas and the carbon dioxide gas are supplied into the cultivating chamber 4 through the pipes 21 and 22. The controller recognizes the oxygen gas concentration in the cultivating chamber 4 through the oxygen gas sensor 23 and also recognizes the concentration of the carbon dioxide gas in the cultivating chamber 4 through the carbon dioxide gas sensor 24. Then, the controller controls the supply amounts of the carbon dioxide gas and the nitrogen gas by controlling the electromagnetic opening/closing valves V1 and V2 so that the concentrations of the carbon dioxide gas, the oxygen gas, and the nitrogen gas in the cultivating chamber 4 become the required concentrations, that is, an atmosphere suitable for cultivation of the culture in the cultivating chamber 4 can be obtained.

The controller monitors the pressure in the cultivating chamber 4 by the pressure sensor 27, and when the pressure in the cultivating chamber 4 becomes higher than a predetermined value, the controller opens an electromagnetic opening/closing valve V35 for the required time and lowers the pressure to a predetermined pressure while a positive pressure more than an outside pressure is maintained.

Moreover, the controller is configured to heat the inside of the cultivating chamber 4 to a required temperature by the heater 25, and by means of control by the controller of an operation of the heater 25 on the basis of the temperature inside the cultivating chamber 4 detected by the temperature sensor 26, the inside of the cultivating chamber 4 is maintained at a required temperature.

Furthermore, in the cultivating chamber 4, steam generated by the supply device 5 is supplied for humidification, and the controller detects the humidity in the cultivating chamber 4 by the humidity sensor 28. Then, if the humidity in the cultivating chamber 4 is higher than a predetermined value on the basis of the humidity detected by the humidity sensor 28, the controller opens the electromagnetic opening/closing valve V9 of the outside air pipe 38 for the required time so that the outside air can be supplied into the cultivating chamber 4. As a result, the inside of the cultivating chamber 4 can be maintained at a required humidity.

As described above, the inside of the cultivating chamber 4 is maintained in the aseptic state by the decontaminating device 6, and the inside of the cultivating chamber 4 is maintained in a suitable environment by the gas supply device 7 and the heater 25. In this state, the loading/unloading work of the container 3 on the racks 13a of the storage cabinets 13A to 13C by the robot hand, not shown, as described above, storage of the container 3 in the storage cabinets 13A to 13C, and the carrying-out work of the container 3 which has been stored and cultivated to the isolator 2 side are performed.

This embodiment is characterized in that steam is generated in the supply device 5 arranged outside the cultivating chamber 4 with the aforementioned constitution as a premise and the steam is supplied into the cultivating chamber 4 so as to humidify the inside of the cultivating chamber 4.

The supply device 5 of this embodiment includes a supply chamber 5A connected to the bottom surface 4E of the cultivating chamber 4 from a lower side of the outside while holding airtightness, a tray 42 installed in this supply chamber 5A and reserving water in the tray 42, and an ultrasonic atomizing device 43 arranged in the supply chamber 5A and having a vibrator inserted into the water in the tray 42. In a side wall of the supply chamber 5A, a tip end portion of a water feed pipe 44 is penetrated while airtightness is held, and the tip end portion of the water feed pipe 44 is located in the tray 42. In the middle of the water feed pipe 44, an electromagnetic opening/closing valve V12 is provided, and the electromagnetic opening/closing valve V12 has its operation controlled by the controller. When the controller opens the electromagnetic opening/closing valve V12 for the required time, it is constituted that water is supplied into the tray 42 through the water feed pipe 44 from a water feed source, not shown.

The bottom surface 4E of the cultivating chamber 4 also serves as a top surface of the supply chamber 5A, and an opening portion 5B is formed at a required position of this top surface. An HEPA filter 45 is mounted on this opening portion 5B. The water in the tray 42 is atomized by the ultrasonic atomizing device 43 and steam is continuously generated, and the steam generated in the supply chamber 5A as described above is passed through the HEPA filter 45 of the opening portion 5B and supplied to the circulation passage 37 in the cultivating chamber 4.

In this embodiment, the steam is generated in the supply chamber 5A provided outside the cultivating chamber 4, and the steam is passed through the HEPA filter 45 of the opening portion 5B and then, supplied into the circulation passage 37 in the cultivating chamber 4.

Subsequently, describing the circulation passage 37 in the cultivating chamber 4, a partition plate 46 is provided covering substantially the whole region of the bottom surface 4E of the cultivating chamber 4 and lower parts of the wall surfaces 4A and 4D front and rear thereof, and a space portion in this partition plate 46 formed between it and the bottom surface 4E and between the wall surfaces 4A and 4D is made the circulation passage 37.

A large number of through holes are drilled in the upper side of the partition plate 46 at positions faced with the both wall surfaces 4A and 4D, and a blow-out port 37A is constituted by the large number of through holes of the partition plate 46 on the wall surface 4A side, while a suction port 37B is constituted by the large number of through holes of the partition plate 46 on the wall surface 4D side.

On a horizontal portion of the circulation passage 37 serving also as the bottom surface 4E, a fan 47 for air circulation is provided at a position closer to the blow-out port 37A side than the HEPA filter 45, and a second HEPA filter 48 is provided in the circulation passage 37 further closer to the blow-out port 37A than the fan 47.

Moreover, a pressure regulating plate 49 is provided in the circulation passage 37 close to the suction port 37B side than the position of the first HEPA filter 45. The pressure regulating plate 49 has a plurality of through holes formed, and the air flowing through the circulation passage 37 flows through the through hole of the pressure regulating plate 49, whereby a flow resistance is applied.

When the fan 47 is operated by the controller, the air is sucked into the circulation passage 37 through the suction port 37B and passes through the pressure regulating plate 49 and further passes through the fan 47 and the HEPA filter 48 via the upper part of the HEPA filter 45 and is finally blown out of the blow-out port 37A. That is, the air in the cultivating chamber 4 is circulated in an arrow direction through the circulation passage 37, and the steam having passed through the HEPA filter 45 and supplied into the circulation passage 37 with that is supplied into the cultivating chamber 4.

In this embodiment, a pressure P1 in a region between the fan 47 and the blow-out port 37A in the circulation passage 37, a pressure P2 in a center part of the cultivating chamber 4, a pressure P3 in a region between the suction port 37B and the pressure regulating plate 49 in the circulation passage 37, a pressure P4 in a region between the pressure regulating plate 49 and the fan 47, and a pressure P5 in the supply chamber 5A are adjusted so as to have a relationship as follows. The pressures in the cultivating chamber 4 are adjusted so that, by an action of the pressure regulating plate 49 and the fan 47, the pressure P1 is the largest, the pressure P2 is smaller than the pressure P1, the pressure P3 is smaller than the pressure P2, and the pressure P4 is smaller than the pressure P3. Thus, the air in the cultivating chamber 4 is circulated in the arrow direction through the circulation passage 37. At that time, dusts are removed by the HEPA filter 48 in the circulation passage 37. Moreover, the pressure P4 is a negative pressure with respect to the pressure P5 in the supply chamber 5A, and the steam generated in the supply chamber 5A is effectively supplied into the circulation passage 37.

As described above, in this embodiment, the supply device 5 is provided outside the cultivating chamber 4, and the steam generated in the supply chamber 5A is passed through the HEPA filter 45 of the opening portion 5B and supplied to the circulation passage 37 of the cultivating chamber 4, whereby the inside of the cultivating chamber 4 can be humidified. Thus, as compared with the prior-art technologies, the constitution inside the cultivating chamber 4 can be simplified, and other facilities for decontamination can be simplified. Thus, the cultivating chamber 4 with a constitution simpler than the prior-art technologies can be provided, and maintenance work of the incubator 1 can be provided. Moreover, the inside of the cultivating chamber 4 can be humidified in a more suitable state while germlessness in the cultivating chamber 4 is maintained.

Moreover, the storage cabinets 13A to 13C in the cultivating chamber 4 can alleviate stress of the culture in the container 3 in the storage cabinets 13A to 13C of this embodiment, as compared with the prior-art incubator constituted such that the storage cabinet itself rotates.

In the aforementioned embodiment, the ultrasonic atomizing device 43 is used as humidifying means but a heater or the like may be used as the humidifying means.

What is claimed is:

1. An incubator comprising:
   an aseptic cultivating chamber for cultivating a culture, the aseptic cultivating chamber comprising a sealable housing, an opening portion provided therein, an air filter provided in the opening portion and a steam supply device provided in a non-aseptic environment outside of the aseptic cultivating chamber for introducing steam into the aseptic cultivating chamber through the air filter, wherein the steam supply device comprises a supply chamber covering the opening portion in the cultivating chamber from the outside, a reserving portion provided in the supply chamber for reserving water and a humidifying device for making steam from the water in the reserving portion.

2. The incubator according to claim 1, wherein the humidifying device is an ultrasonic atomizer for atomizing water.

3. The incubator according to claim 1, wherein
   a circulation passage for circulating air in the aseptic cultivating chamber in a certain direction is provided in the aseptic cultivating chamber, the steam having passed through the air filter is supplied to the circulation passage, and the pressure in a region where the steam having been passed through the air filter in the circulation passage is supplied is adjusted to be lower than a pressure in the steam supply device.

4. The incubator described in claim 3, wherein
   the humidifying device is an ultrasonic atomizing device for atomizing water.

\* \* \* \* \*